(12) United States Patent
Katayama (10) Patent No.: US 8,496,635 B2
(45) Date of Patent: Jul. 30, 2013

(54) CONTAINER WITH A SQUEEZED NOZZLE AND LEVER

(76) Inventor: Ryu Katayama, Tokyo (JP)

( * ) Notice: Subject to any disclaimer, the term of this patent is extended or adjusted under 35 U.S.C. 154(b) by 95 days.

(21) Appl. No.: 13/004,539

(22) Filed: Jan. 11, 2011

(65) Prior Publication Data

US 2011/0106024 A1  May 5, 2011

Related U.S. Application Data

(63) Continuation of application No. PCT/JP2009/062665, filed on Jul. 13, 2009.

(30) Foreign Application Priority Data

Jul. 14, 2008  (JP) ................................. 2008-182441

(51) Int. Cl.
  *A61M 11/00*  (2006.01)
  *B65D 47/22*  (2006.01)
  *B65D 47/18*  (2006.01)

(52) U.S. Cl.
  CPC ............. *A61M 11/00* (2013.01); *B65D 47/18* (2013.01)
  USPC .................. 604/298; 222/207; 128/200.14

(58) Field of Classification Search
  USPC ................ 604/294–302; 222/207, 420, 422
  See application file for complete search history.

(56) References Cited

U.S. PATENT DOCUMENTS

| 2,219,604 | A | * | 10/1940 | Trotter | 222/207 |
| 2,734,665 | A | * | 2/1956 | Flamm | 222/207 |
| 2,811,283 | A | * | 10/1957 | Bowen | 222/109 |
| 3,366,284 | A | * | 1/1968 | Marona et al. | 222/211 |
| 3,552,605 | A | * | 1/1971 | Hein | 222/207 |
| 3,645,423 | A | * | 2/1972 | DeGraw | 222/207 |
| 3,756,732 | A | * | 9/1973 | Stoffler | 401/202 |
| 3,822,720 | A | * | 7/1974 | Souza | 137/846 |
| 4,111,200 | A | * | 9/1978 | Sbarra et al. | 604/298 |
| 4,553,686 | A | * | 11/1985 | Dougherty | 222/212 |

(Continued)

FOREIGN PATENT DOCUMENTS

| EP | 2003069 A2 | 12/2008 |
| JP | 13045 | 5/1909 |

(Continued)

OTHER PUBLICATIONS

International Search Report dated Oct. 13, 2009 for corresponding International Patent Application No. PCT/JP2009/062665 (with English translation).

*Primary Examiner* — Melanie Hand
*Assistant Examiner* — Paula Craig
(74) *Attorney, Agent, or Firm* — Ohlandt, Greeley, Ruggiero & Perle, L.L.P.

(57) ABSTRACT

A container includes a nozzle having rubber elasticity in a constriction part, and a lever for nipping the nozzle indirectly. The nozzle has a storage part, a base, and a valve. The storage part is provided in the constriction part, and is intercepted with the main body by contacting inner walls at the communicating part when the nozzle is nipped and flattened by the lever. The valve is opened when the internal pressure of the storage part exceeds predetermined pressure while operated state and spouts liquid in the storage part. The constriction part expands by being nipped with the lever until the internal pressure of the storage part reaches to predetermined pressure. Liquid in the storage part is jetted since the constriction part shrinks by the rubber elasticity when the valve is released.

6 Claims, 5 Drawing Sheets

U.S. PATENT DOCUMENTS

| | | | |
|---|---|---|---|
| 4,568,004 A * | 2/1986 | Goncalves | 222/207 |
| 4,792,334 A * | 12/1988 | Py | 604/301 |
| 5,069,675 A * | 12/1991 | Menchel et al. | 604/295 |
| 5,261,571 A * | 11/1993 | Goncalves | 222/214 |
| 5,356,039 A * | 10/1994 | Christine et al. | 222/107 |
| 5,578,020 A * | 11/1996 | Mosley | 604/295 |
| 5,582,330 A * | 12/1996 | Iba | 222/212 |
| 5,810,794 A * | 9/1998 | Peplinski | 604/295 |
| 6,168,581 B1 * | 1/2001 | Buehler | 604/295 |
| 6,595,970 B1 * | 7/2003 | Davidian | 604/300 |
| 6,814,265 B2 * | 11/2004 | Clifford et al. | 222/420 |
| 7,353,971 B2 * | 4/2008 | Stradella | 222/162 |
| 7,635,070 B2 * | 12/2009 | Cohen et al. | 222/162 |
| 2002/0190079 A1* | 12/2002 | Hamamoto | 222/105 |
| 2002/0193757 A1* | 12/2002 | Benktzon et al. | 604/301 |
| 2005/0131358 A1* | 6/2005 | Skolik | 604/295 |
| 2009/0137972 A1 | 5/2009 | Katayama | 604/295 |
| 2009/0318883 A1 | 12/2009 | Sugahara et al. | 604/298 |

FOREIGN PATENT DOCUMENTS

| | | |
|---|---|---|
| JP | 13-3803 | 10/1924 |
| JP | 62-120859 | 6/1987 |
| JP | 2-23381 | 2/1990 |
| JP | 5-34663 | 9/1993 |
| JP | 6-292703 | 10/1994 |
| JP | 2000-210368 | 8/2000 |
| JP | 2002-191671 | 7/2002 |
| JP | 2004-148052 | 5/2004 |
| JP | 2004-210313 | 7/2004 |
| JP | 2005-335773 | 12/2005 |
| JP | 200818987 A * | 1/2008 |
| WO | WO 2007/111256 A1 | 10/2007 |

* cited by examiner

CONTAINER WITH A SQUEEZED NOZZLE AND LEVER

CROSS REFERENCE TO RELATED APPLICATIONS

This is a Continuation Application of PCT Application No. PCT/JP2009/062665, filed Jul. 13, 2009, which was published under PCT Article 21(2) in Japanese.

This application is based upon and claims the benefit of priority from prior Japanese Patent Application No. 2008-182441, filed Jul. 14, 2008, the entire contents of which are incorporated herein by reference.

BACKGROUND OF THE INVENTION

1. Field of the Invention

The present invention relates to a container comprising a lever to squeeze a nozzle and the nozzle that does not drop an internal liquid but spouts by the shrinkage force of rubber elasticity.

2. Description of the Related Art

The installation container of the method to drop liquid medicine is disclosed in Japanese Examined utility model specification No. 13045 (Patent document 1), Japanese The Taisho 13 utility-model-application public notice No. 3803 after examination gazette in 1924 (Patent document 2), Jpn. Pat. Appin. KOKAI Publication No. JP S62-120859 A (Patent document 3), JP H05-34663 Y (Patent document 4), and JP 2005-335773 A (Patent document 5). These instillation containers are made upside-down so that the nozzle may turn below and used. When the user presses a container, liquid medicine flows out from the nozzle and is dropped. Therefore, the user comes to look up at the liquid medicine dropped to apply eyewash.

In the instillation container shown in patent documents 1-5, it should become accustomed to drop liquid medicine to the eyeball well with it saw right above. When it is difficult for the body to face up, liquid medicine cannot be dropped well. Since a mouth may open reflectively when facing up, it is shameful when appearance applied eyewash is seen by others. Then, the eye medicine container to supply liquid medicine to eyes without face uping is indicated in Jpn. Pat. Appin. KOKAI Publication No. JP H06-292703 A (Patent document 6), JP 2002-191671 A (Patent document 7), and JP 2004-148052 A (Patent document 8).

Since the hand moves When pressing a button with one's finger to make liquid medicine blow off, it is difficult to atomize well to eyes with the spraying type eyedropper described in patent document 6.Since the nozzle of the eye medicine container described in patent documents 7 and 8 is always opened, the internal pressure that jets liquid medicine is insufficient, and liquid medicine drips from the nozzle if the container is not instantaneously pushed by the fingers.

Moreover, both of the eye medicine containers described in patent documents 6 and 8 require a complex mechanism, and are uneconomical as the container made disposable from the aspect of good hygiene.

BRIEF SUMMARY OF THE INVENTION

Present invention provides a container with a squeezed nozzle and a lever, the container spouts an internal liquid from the nozzle without depending on the posture of the container, and is manufactured at a low price the structure is simple.

A container with squeezed nozzle and a lever according to the present invention comprises a main body which has an opening and accumulates a liquid internally, a nozzle which is installed in the opening and has a rubber elasticity in a constriction part on a tip side, a lever which is arranged adjacent to the constriction part to nip the constriction part indirectly, and a cap which installed removable covering the nozzle.

The nozzle has a storage part, a base, and a valve. The storage part is provided into the constriction part, and leads with the inside of the main body in a free state from which the constriction part is not nipped with the lever. A communicating passage between the storage part and the inside of the main body is intercepted by abutting the inner walls opposed in a passage between the storage part and the inside of the main body with operated condition that the constriction part is nipped and flatted with the lever. The base engages with the opening, and has a liquid supply path that runs from the opening to the storage part. The valve is opened when an internal pressure of the storage part exceeds predetermined pressure while operated state, and makes the liquid in the storage part spout. The constriction part of the nozzle expands with the internal pressure of the storage part until the pressure reaches to predetermined pressure by being nipped with the lever while operated state.

The lever is displaced from a first posture to a second posture when the lever is operated. In the first posture, the lever shuts the storage part from the main body by flatting the constriction part and fitting the inner walls which are opposing with each other at the communicating part between the inside of the main body and the storage part. In the second posture, the lever makes the constriction part flat so as to squeeze the storage part toward the valve while maintaining the state to intercept between the main body and the storage part.

In the container with the squeezing nozzle and the lever comprising the above-mentioned composition, the lever has a proximal portion which is fastened beneath the main body, a standing-up portion which extends from the proximal portion, a handling portion which is turned in a direction away from the nozzle on a tip side of the nozzle, and a contacting portion which is facing to the constriction part extending from the operating portion toward the constriction part turning around the standing-up portion. In this case, the lever may be installed in the couple at the position of symmetry where place on either side of the constriction part.

In the container with the squeezing nozzle and the lever comprising the above-mentioned composition, the nozzle has a protrusion which blocks between the liquid supply path and the storage part when the lever flats the constriction part.

In the container with the squeezing nozzle and the lever comprising the above-mentioned composition, the valve may be a pinhole which is shut up the internal pressure of the storage part to airtight below predetermined pressure, and is expanded and spouts the liquid in the storage part when the internal pressure exceed the predetermined pressure.

A slit which has width according to the spouting direction that the liquid passes, shuts up into the airtight when the internal pressure of the storage part is below a predetermined pressure, and is opened when the internal pressure of the storage part exceeds the predetermined pressure, or cross shape intersecting of the slit are acceptable as the shape of the valve except that it is a pinhole.

The cap may have a locking part which obstructs the displacement of the lever to the second posture while attached condition.

"Spout" means the liquid becomes a spray and flies from the tip of the nozzle in this Specification. The spray at this time is a droplet which is smaller than a liquid measure of one drop when the liquid is dropped by its own weight.

The container with the squeezing nozzle and the lever according to the present invention comprising the above-mentioned structure spouts the liquid stored in the main body from the nozzle by defying gravity. In this case, the liquid becomes a spray and is jetted out from the nozzle.

When the container with the squeezing nozzle and the lever according to the present invention is used as an eye medicine container, liquid medicine can be supplied to eyes even if user's posture is forward or downward. This container can spout the content liquid from the nozzle without it is influenced by gravity. Therefore, this container is not only used as an eye medicine container for the person who is difficult to face up to supply liquid medicine to eyes, but also used as an eye medicine container in a zero gravity space.

Since the structure of the container is manufactured simply and at a low price, the container with the nozzle and the lever of the present invention is suitable as the eye medicine container for the sanitary use throwing away.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
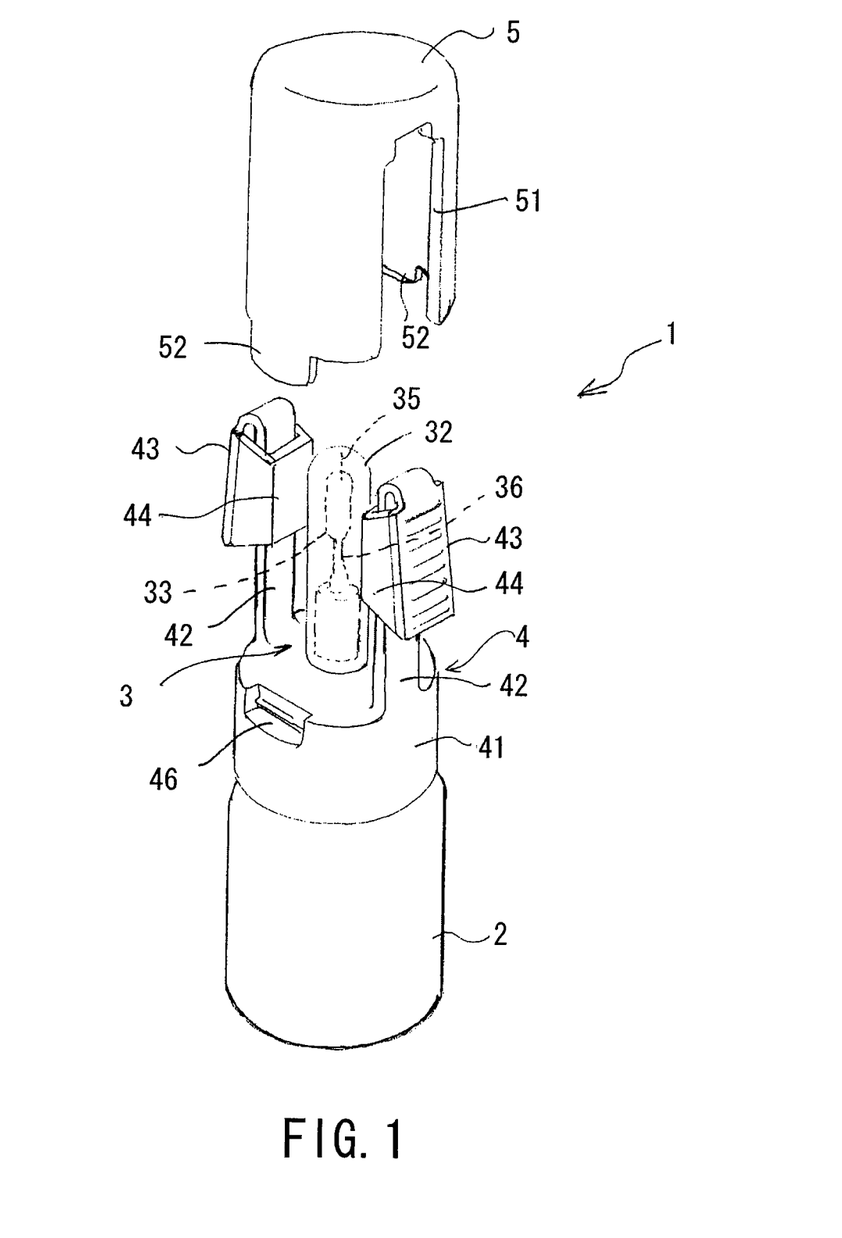
FIG. 1 is perspective view showing the container with the squeezing nozzle and the lever according to the first embodiment of the present invention.

A container 1 of the first embodiment according to the present invention will be described referring to FIGS. 1-7 as an example of the case where it is used as an eye medicine container. The container 1 shown in FIG. 1 is a container with a squeezing nozzle and lever, the container 1 has a main body 2, a nozzle 3, a lever 4, and a cap 5. The main body 2 has an opening 21, and accumulates liquid L, which is liquid medicine, in an inside. It is preferable that the main body 2 is formed with the material which is not deteriorated by internal liquid L, and does not ruin the purity of this liquid L by not eluting contents of material to liquid L, for instance, by the glass, plastic such as polypropylenes, and the alloy such as aluminum.

Figure 2:
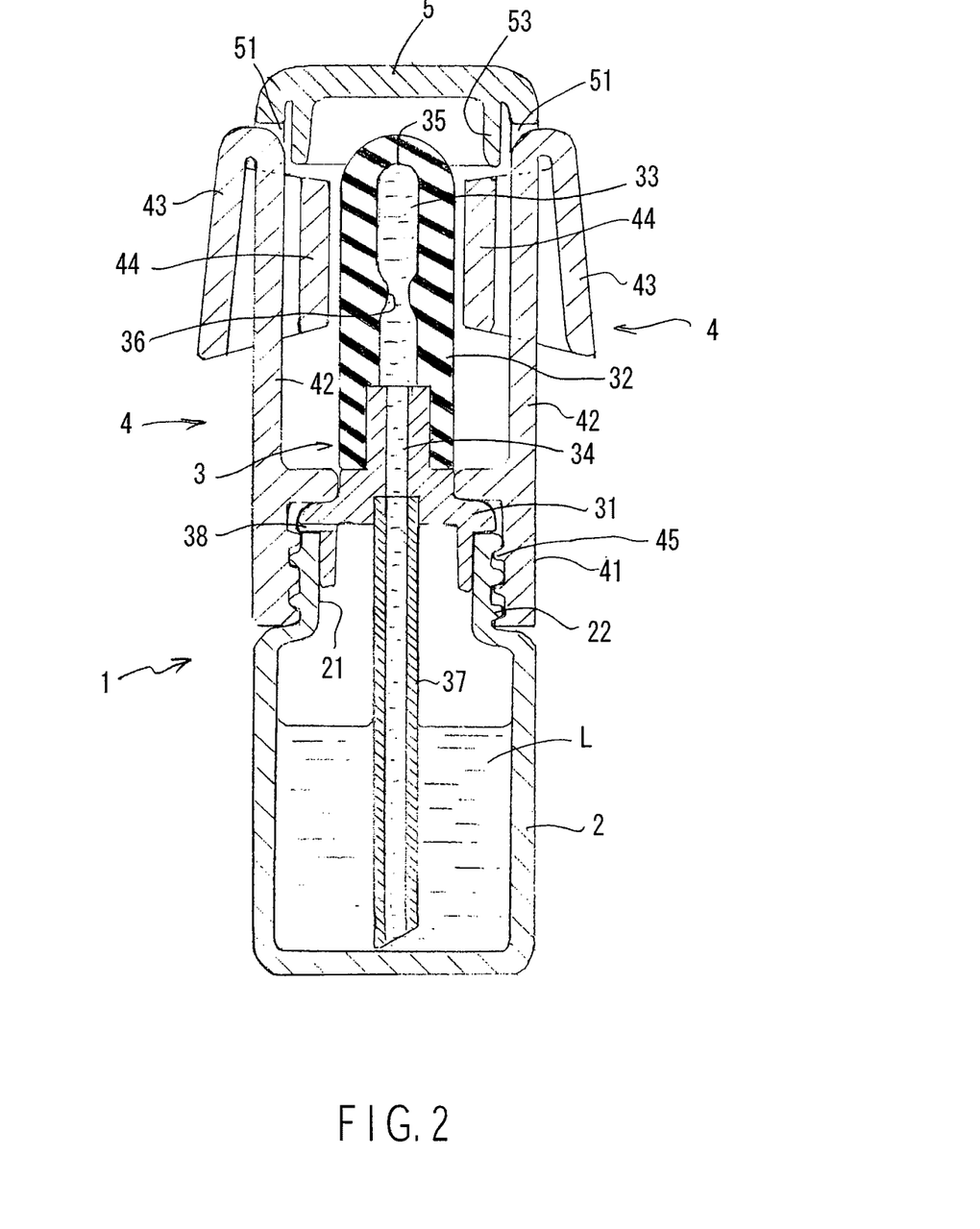
FIG. 2 is a cross sectional view of the container with the squeezing nozzle and the lever shown in FIG. 1.

Nozzle 3 is installed in opening 21, and has a constriction part 32 with rubber elasticity on a tip side as shown in FIG. 2. After liquid L is inserted in the main body 2, the nozzle 3 is fastened by the method not to drop out of opening 21 easily. In this embodiment, the nozzle 3 is pressed in to the opening 21 of main body 2 and engages. It may bond after it pressed in, or it may fuse together mutually by the laser and the supersonic wave when the main body 2 and the nozzle 3 are plastics.

The lever 4 is adjacent to the constriction part 32 of the nozzle 3 so as to nip the constriction part 32 indirectly. The cap 5 has shape with which nozzle 3 is covered as shown in FIG. 1, and is installed removable. When this container 1 is carried, the cap 5 doesn't drop out easily and have to be able to protect the nozzle 3. Therefore, the cap 5 may be formed in externally engaged to the main body 2, the nozzle 3 or the lever 4.

Nozzle 3 is composed of a base 31 and a constriction part 32 as shown in FIG. 2, and a storage part 33, a liquid supply path 34, a valve 35, and a protrusion 36 are formed. The base 31 engages with opening 21, and has the liquid supply path 34 which runs from the opening 21 to storage part 33. The constriction part 32 is set in the base 31 in the opposite side of the main body 2. The constriction part 32 is formed with excellent material in the restoration, such as silicone rubber and Urethane elastomer, in case of flatness repeatedly. The constriction part 32 is set so as not to come off from the base 31 or is formed the difference and engages it. The constriction part 32 may not only be engaged to the base 31 but also be fastened with the adhesive or be fused together by the laser and the ultrasonic wave so as to become liquid tight. Moreover, the integrally injecting plastic operation is performed for the base 31 with hard material and for the constriction part 32 with soft material.

A conduit tube 37, which has length reaching the bottom of the main body 2, is installed beneath the opening 21 of the liquid supply path 34. The liquid supply path 34 is formed more thinly than the storage part 33 to make liquid L that entered the storage part 33 remain as it is in the storage part 33 according to the surface tension of the liquid L. Moreover, the base 31 has a communicating hole 38 to make internal pressure of the main body 2 an atmospheric pressure. It is also desirable that the communicating hole 38 is covered with the semi-permeable membrane that does not pass the liquid L though the gas is passed.

The storage part 33 is formed in constriction part 32. The communication between the storage part 33 and the inside of the main body 2 is maintained while a free state and is intercepted while an operated state. The free state is the state in which the lever 4 does not nip the constriction part 32. The operated state is a state in which the lever 4 nips and is flatten the constriction part 32.

The valve 35 is a pinhole, and it is installed in the tip of the constriction part 32 of the opposite side in the base 31. The valve 35 becomes narrower and is sealed up to the airtight when the inner pressure of storage part 33 is below predetermined pressure. Since the valve 35 deforms elasticity and is expanded when the constriction part 32 becomes the operated state and the internal pressure of the storage part 33 exceeds the predetermined pressure, the valve 35 spouts the liquid L stored in storage part 33.

When the constriction part 32 is nipped and flattened with the lever 4 until the internal pressure of storage part 33 reaches the pressure at which the valve 35 is opened while the operated state, the part of the constriction part 32 that does not touch the lever 4 is expanded. The pressing force added with the lever 4 after the protrusion 36 blockades the liquid supply path 34 is accumulated as a shrinkage force of the rubber elasticity caused the constriction part 32 is expanded. Enlarged stricture part 32 shrinks by the rubber elasticity when the internal pressure of the storage part 33 rises and the valve 35 is opened. As a result, the liquid L in the storage part 33 is spouted in great force through the valve 35.

Figure 5:
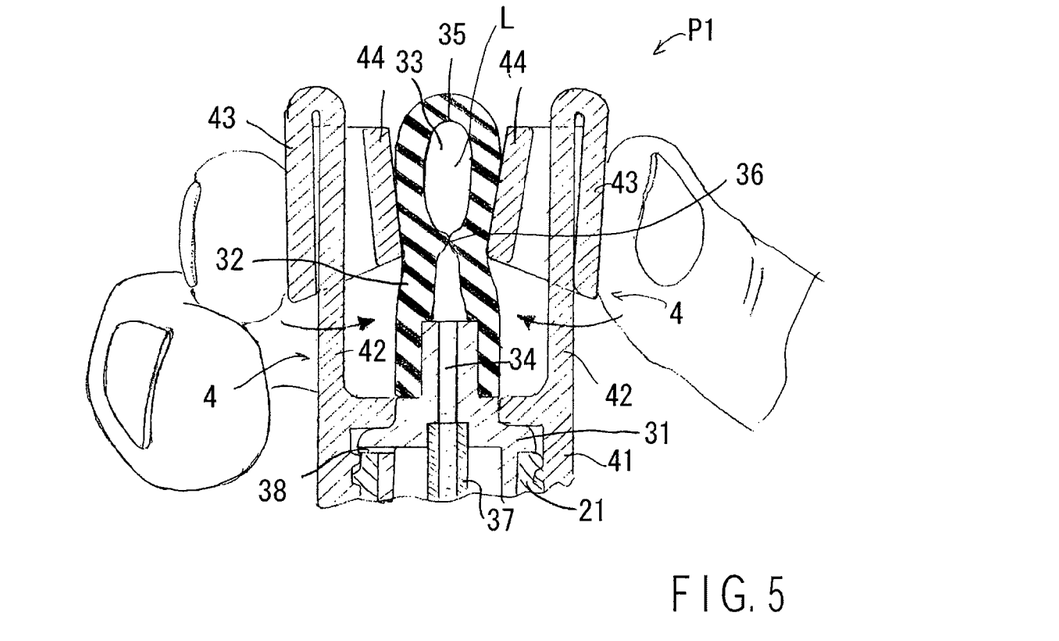
FIG. 5 is cross-sectional view in the state operated in the first posture for the lever of the container with the squeezing nozzle and the lever shown in FIG. 1.
Figure 6:
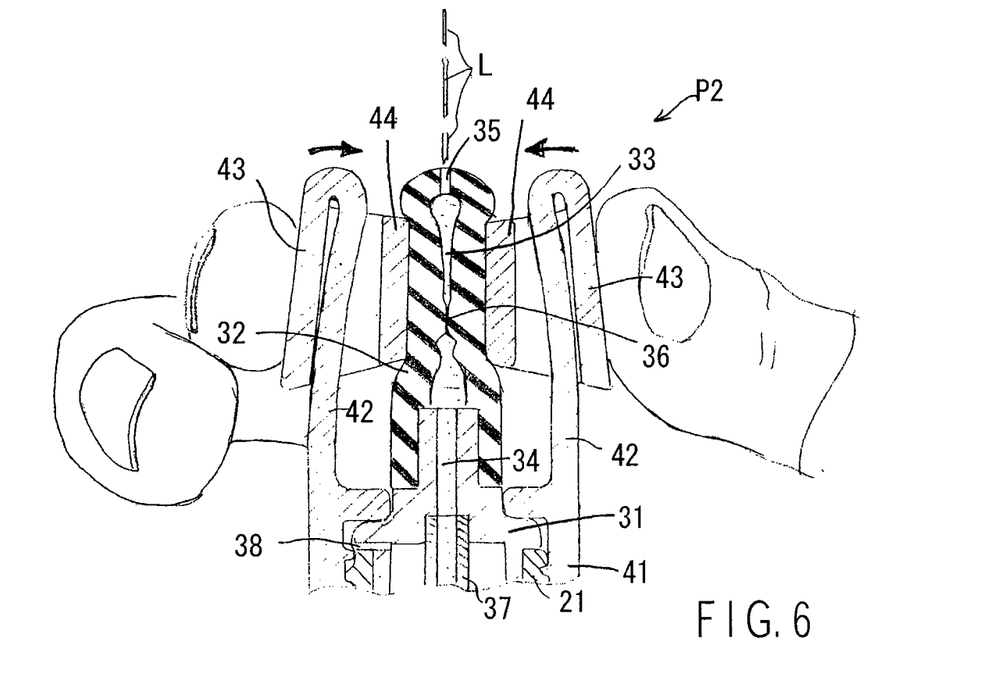
FIG. 6 is cross-sectional view in the state operated in the second posture for the lever of the container with the squeezing nozzle and the lever shown in FIG. 5.

The protrusion 36 is formed between the storage part 33 and the liquid supply path 34. The protrusion 36 blockades between the storage part 33 and the liquid supply path 34 and intercepts the flow when the constriction part 32 is nipped and is flattened with the lever 4 as shown in FIGS. 5 and 6. Since the protrusion 36 is formed, it can blockade between the storage part 33 and the liquid supply path 34 even by small power. If the communicating path between the storage part 33 and the liquid supply path 34 is shut by completely contacting the inner walls in the part between the storage part 33 and the liquid supply path 34 when the constriction part 32 is flattened by the lever 4, the protrusion 36 is not indispensable to the constriction part 32.

Figure 3:
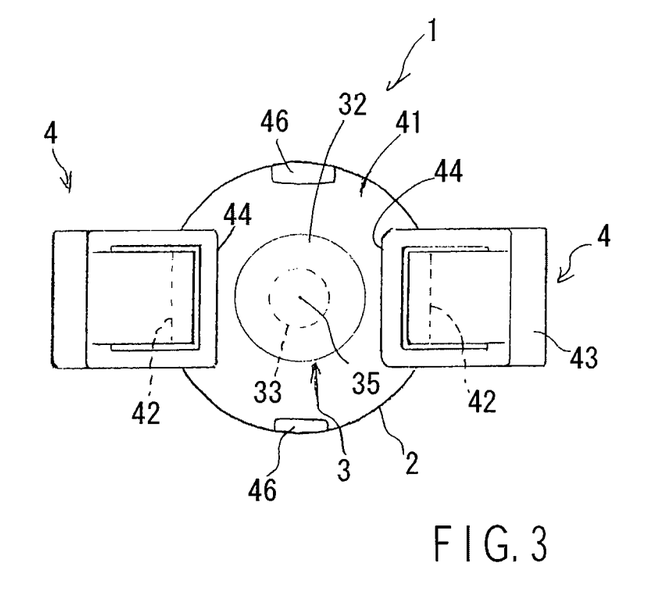
FIG. 3 is a plan view of the container with the squeezing nozzle and the lever in FIG. 1 seen from a nozzle tip side.

The lever 4 is arranged in the couple at the position that becomes symmetry placed among the nozzle 3 as shown in FIGS. 1 through 3. The lever 4 comprises a proximal portion 41, a standing up part 42, a handling portion 43, and contact portion 44. The proximal portion 41 is formed to a ring shape that encloses the base 31 of the nozzle 3 in this embodiment at the continuity. The proximal portion 41 has female screw 45 internally, and is fastened in the main body 2 by being screwed together to a male screw 22 in outer peripheral of the opening 21 of the main body 2.

Figure 4:
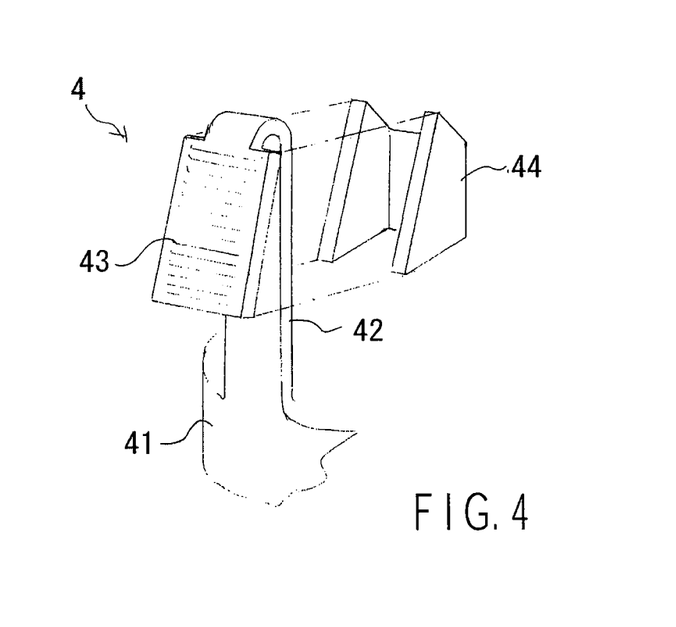
FIG. 4 is exploded perspective view of the lever of the container with the squeezing nozzle and the lever shown in FIG. 1.

The standing up part 42 is extending in parallel to the constriction part 32 toward the valve 35. The handling portion 43 connects with the standing up portion 42 on a tip side of the nozzle 3, and is turned into the direction away from the constriction part 32. A lot of bump for the skid is formed on the surface of handling portion 43. The contacting portion 44 extends from the both sides edge of the handling portion 43 turning round the standing up portion 42 toward the constriction part 32, and faces to the constriction part 32. The contacting portion 44 is manufactured separately from the standing up portion 42 and the handling portion 43 and is bonded or is fused together as shown in FIG. 4. It is also possible that the lever 4 is integrally injected plastic operation by devising a combination of the metal mold.

The contacting portion 44 is formed in a range from a part of this side of the valve 35 of the storage part 33 to the protrusion 36. A part of the contacting portion 44 beneath the protrusion 36 is away from the handling portion 43 than a part of the contacting portion 44 beneath the valve 35 as shown in FIG. 2. As a result, the contacting portion 44 beneath the protrusion 36 comes into contact with the constriction part 32 in first when the lever 4 is operated.

The lever 4 which has the above-mentioned structure is operated by the user so as to nip the constriction part 32 by the finger indirectly. The lever 4 is displaced from the first posture P1 shown in FIG. 5 to the second posture P2 shown in FIG. 6 by being operated. Since the lever 4 flats the constriction part 32 in the first posture P1, the storage part 33 is separated from the main body 2 by being intercepted between the constriction part 32 and the main body 2. The lever 4 makes the constriction part 32 flat in the second posture P2 so as to squeeze up the storage part 33 toward the valve 35 maintaining a state in which a part between the storage part 33 and the main body 2 is intercepted.

In a word, when the lever 4 is operated, the handling portion 43 and the contacting portion 44 swing toward the constriction part 32 around a jointed portion of the standing up portion 42 and the handling portion 43, and the lever 4 becomes the first posture P1. Since the protrusion 36 abuts to the constriction part 32, the standing up portion 42 of the lever 4 bends as the beam where the proximal portion 41 is assumed to be fixed end when force is further added to the lever 4. Therefore the lever 4 becomes the second posture P2 after the contacting portion 44 flats the constriction part 32 squeezing the storage part 33 toward the valve 35.

The valve 35 is shut until the internal pressure of the storage part 33 exceeds predetermined pressure while the lever 4 is displacing from the first posture P1 to the second posture P2. Therefore, the deforming force added to the constriction part 32 with the lever 4 is accumulated in the constriction part 32 as a shrinkage force caused since a part of the constriction part 32 where does not touch the lever 4 expands.

The valve 35 opens as shown in FIG. 6 when the internal pressure of storage part 33 exceeds predetermined pressure at which the valve 35 is opened, and liquid L stored in the storage part 33 spouts mightily according to the shrinkage force has been accumulated by the rubber elasticity of expanding the constriction part 32. Liquid L becomes a small amount of spray from one drop dropped by its own weight and it flies from the tip of nozzle 3 since liquid L jets mightily.

When pressure in the storage part 33 decreases more than predetermined pressure, the valve 35 is closed by the elastic force. When liquid L that exists in the storage part 33 is spouted, the valve 35 is naturally shut even if the second posture P2 in which the constriction part 32 is nipped with lever 4 is maintained. When the lever 4 returns by releasing one's hold, and the constriction part 32 is restored in the free state, liquid L that exists in the main body 2 is sucked up to the storage part 33 through the conduit tube 37.

The cap 5 has notches 51 and hooks 52. The notches 51 are arranged in two places corresponding to the lever 4 to engage with the lever 4. The hook 52 is installed between two notches 51 respectively, and connected with a concave part 46 formed in the base 41 of the lever 4. When the proximal portion 41 of the lever 4 is pressed to deform the cap 5, the hook 52 is released from concave part 46. Moreover, the cap 5 comprises a protecting part 53 internally as shown in FIG. 2. The protecting part 53 supports a tip side of the standing up parts 42 so that the lever 4 should not become the second posture P2.

Figure 7:
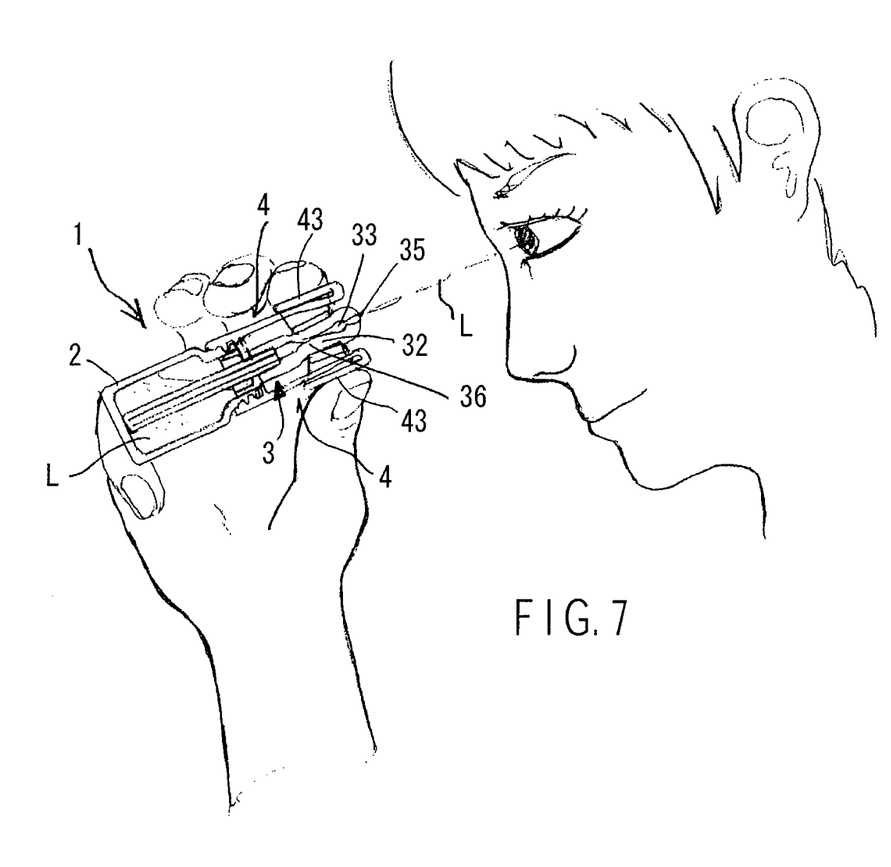
FIG. 7 is cross-sectional view of the container with the squeezing nozzle and the lever shown in FIG. 1 in the state using as an eye medicine container.

The container 1 as mentioned above composed can spout liquid L from the tip of the nozzle without it is influenced by gravity. Therefore, the user can supply liquid medicine to eyes by using the container, even in the state that turns to the front as shown in FIG. 7 and the state of the face down in addition. Since it need not face up, the person to whom face-up is difficult can easily supply the eye medicine. Moreover, it is also easy to supply the eye medicine to the pet. In addition, even if it is a microgravity environment such as outer space, the eye medicine can be supply by using the container.

Liquid L in the storage part 33 is spouted by the shrinkage force that originates in the rubber elasticity force of the constriction part 32. Therefore, the capacity of storage part 33 can be spouted by making liquid L a spray even if liquid L is a small amount that is less than one drop dropped by its own weight. Since liquid L is spouted in great force, liquid L can be prevented from dripping because of the tip of nozzle 3.

When the receptacle of this invention was made for trial purposes, it was confirmed that liquid L spouted from nozzle 3 flew from nozzle 3 in the straight line by about 15 cm or more.

The container with a squeezing nozzle and the lever of the present invention can be used as a container where the liquid of a minute amount less than one drop when the storage liquid is dropped is spouted, and the liquid of minute amount is spouted fighting against gravity, besides an eye medicine container, a container for perfume, and a liquid seasoning container.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A container with squeezing nozzle and lever comprising:
   a main body comprising an opening and stores liquid in an inside volume of the main body;
   a nozzle which is installed in the opening having a proximal end disposed near the opening and a distal end disposed away from the opening, the nozzle comprising a constriction part having rubber elasticity on the distal end;
   a pair of levers which are symmetrically arranged adjacent to the constriction part to nip the constriction part; and
   a cap which is removably installed and configured to cover the nozzle,
   wherein the nozzle comprises:
   a storage part which is formed in the constriction part, the storage part communicating with the inside volume of the main body in a free state in which the constriction part is not nipped with the pair of levers, and the storage part not communicating with the inside of the main body in an operated state in which the constriction part is being nipped and flattened with the pair of levers, flow of the liquid from the main body to the storage part in the operated state being stopped by contacting opposed inner walls of the storage part by the pair of levers in the operated state;
   a base which is fastened to the opening and comprising a liquid supply path which runs from the opening to the storage part; and
   a valve at a tip portion of the distal end of the nozzle which is opened when an internal pressure of the storage part exceeds a predetermined pressure when the storage part is being nipped and flattened with the pair of levers, the nipping and flattening causing the liquid in the storage part to spout through the valve.

2. The container with squeezing nozzle and lever of claim 1, wherein each of the levers comprises:
   a proximal portion which is fastened on the base of the nozzle;
   a straight portion which is extended from the proximal portion as a cantilever;
   a handling portion which is swingably connected to a distal end of the straight portion extending toward the proximal portion and disposed opposite to the constriction part; and
   a contacting portion which is inserted between the constriction part and the straight portion extending from the handling portion to move together with the handling portion.

3. The container with squeezing nozzle and lever of claim 1, wherein the nozzle comprises: a protrusion configured to block the flow of liquid between the liquid supply path and the storage part when the pair of levers flatten the constriction part.

4. The container with squeezing nozzle and lever of claim 1, wherein the valve is a pinhole which is configured to close in an airtight manner to hold the internal pressure of the storage part below predetermined pressure and is configured to be expanded to allow the liquid stored in the storage part to spout when the internal pressure exceeds the predetermined pressure.

5. The container with squeezing nozzle and lever of claim 1, wherein the lever is configured to be displaced from a first posture to a second posture during the operated state, wherein in the first posture, the storage part is shut and prevented from communicating with the main body by contacting protrusion parts opposing each other inside the constriction part and flattening the constriction part, and wherein in the second posture, the constriction part is further flattened so as to squeeze liquid in the storage part toward and through the valve.

6. A container with squeezing nozzle and lever comprising:
   a main body with an opening configured to store liquid in an inside volume of the main body;
   a nozzle comprising a base fastened to the opening, a constriction part with rubber elasticity extending from the base, a storage part formed in the constriction part communicating with the inside of the main body through a liquid supplying path provided in the base, and a valve formed at a tip portion of the constriction part as a pinhole;
   a pair of levers symmetrically arranged on the base corresponding to the constriction part, each of the levers comprising a proximal portion fastened on the base, a straight portion extending from the proximal portion as a cantilever parallel with the constriction part, a handling portion placed opposite the constriction part and swingably connected to a distal end of the straight portion, and a contacting portion inserted between the constriction part and the straight portion and connected to the handling portion to move together with the handling portion;
   wherein the storage part communicates with the inside of the main body when the constriction part is not nipped with the pair of levers, and does not communicate with the inside of the main body when the constriction part is nipped with the pair of levers in an operated state causing inner walls of the liquid supply path to contact each other in an airtight manner when the constriction part is nipped and flattened with the pair of levers by swinging the contacting portion with the distal end as a fulcrum;
   the tip portion of the constriction part is expanded with internal pressure of the storage part by gradually squeezing the constriction part from a proximal portion toward the tip portion so as to bend the straight portion when the internal pressure is less than a predetermined pressure while the storage part is in the operated state; and
   the valve is opened when the internal pressure of the storage part exceeds a predetermined pressure while the storage part is in the operated state, to spout the liquid in the storage part by a compressive force generated by the squeezing of the rubber elasticity of the constriction part.

* * * * *